United States Patent [19]

Tramount

[11] Patent Number: 5,136,055
[45] Date of Patent: Aug. 4, 1992

[54] METHOD FOR PRODUCTION OF DICARBOXYLIC ACID AND LACTONE

[75] Inventor: Yvette A. Tramount, Charleston, S.C.

[73] Assignee: Westvaco Corporation, New York, N.Y.

[21] Appl. No.: 754,070

[22] Filed: Sep. 3, 1991

[51] Int. Cl.$^5$ .................... C07D 313/00; C07C 63/14
[52] U.S. Cl. .................... 549/266; 549/273; 549/295; 549/328; 562/480; 562/486
[58] Field of Search ............... 549/266, 273, 295, 328; 562/480, 486

[56] References Cited

U.S. PATENT DOCUMENTS

| | | | |
|---|---|---|---|
| 2,278,309 | 3/1942 | Freeman | 260/419 |
| 2,313,636 | 3/1943 | Freeman | 260/419 |
| 3,753,968 | 8/1973 | Ward | 260/97.6 |

OTHER PUBLICATIONS

"Double-Solvent (Fractional) Extraction," Perry, R. H. and Chilton, C. H., *Chemical Engineers' Handbook*, 5th Edition, 1973, pp. 15-23, 24.
"Industrial Utilization of C21 Dicarboxylic Acid," Benjamin F. Ward et al., The Journal of the American Oil Chemicals Society, vol. 52, Jul. 1975, pp. 291–224.
"New Solvent System for Separation of Fatty Acids $C_{10}$–$C_{18}$ by Countercurrent Distribution," Will Fritz, III, *Analytical Chemistry*, vol. 33, No. 4, Apr. 1961, pp. 647–648.
"Polymerization, Copolymerization, and Isomerization," J. P. Cowan, *The Journal of the American Oil Chemicals Society*, vol. 31, Nov. 1954, pp. 529–535.

Primary Examiner—C. Warren Ivy
Assistant Examiner—Ba K. Trinh
Attorney, Agent, or Firm—Daniel B. Reece, IV; Terry B. McDaniel; Richard L. Schmalz

[57] ABSTRACT

A 21-carbon aliphatic branched chain dicarboxylic acid and a 21-carbon lactone are produced by reacting fatty acid (which contains linoleic acid) with acrylic acid via iodine catalysis, and subsequently removing from the low monomer reaction product the resulting C-21 lactone via solvent extraction with acetonitrile and hexane or heptane. The reaction products are distilled to yield dicarboxylic acid and lactone of high purity.

3 Claims, No Drawings

METHOD FOR PRODUCTION OF DICARBOXYLIC ACID AND LACTONE

FIELD OF INVENTION

This invention relates to the production of a dicarboxylic acid and a lactone each having 21 carbon atoms. In particular, this invention relates to making a high purity C-21 dicarboxylic acid via the novel process of removing the C-21 lactone byproduct from the low monomer reaction product of iodine catalysis of acrylic acid and fatty acid (which contains linoleic acid) via solvent extraction with acetonitrile and hexane or heptane.

BACKGROUND OF THE INVENTION

Several applications have been developed for derivatives of dicarboxylic acid in the fields of coatings, detergents, and corrosion inhibitors. As used herein the term "dicarboxylic acid" is intended to mean a dicarboxylic acid having 21 carbon atoms (see FIG. 1), but in some instances it includes minor amounts of dicarboxylic acid of other molecular weights. The versatility these materials exhibit in meeting the requirements of a variety of product applications is evidenced by their widespread use in commerce.

It is known in the art to react conjugated linoleic acid with certain dienophiles or activated mono-olefins to produce various polyfunctional Diels-Alder adducts. It is also known that the reactivity of the conjugated linoleic acid is determined by its geometrical isomerism about the double-bond system; and that the preferred reactive isomer has a trans-trans configuration. As demonstrated by the article, "Polymerization, Copolymerization, and Isomerization", J. C. Cowan, *The Journal of the American Oil Chemicals Society*, Vol. 31, November 1954, pp. 529-535, it has long been recognized that a variety of catalysts (such as iodine, sodium or potassium bisulfates, sulfur, selenium, noble metals, and the like) can be used to isomerize the cis-trans isomers into the trans-trans state, thereby inducing these cis-trans isomers of conjugated linoleic acid to react in a Diels-Alder reaction.

The method preferred by industry for the production of dicarboxylic acid is taught in commonly assigned U.S. Pat. No. 3,753,968, which is hereby incorporated by reference. There, a fatty acid mixture containing both conjugated and non-conjugated linoleic acid is simultaneously reacted with acrylic acid in the presence of an iodine catalyst to produce a fatty acid mixture containing dicarboxylic acid. This mixture is subsequently distilled to recover a linoleic free fatty acid fraction and a dicarboxylic acid fraction.

At the time this process was patented, it was believed that the amount of dicarboxylic acid formed was approximately the same as the starting content of linoleic acid in the fatty acid mixture. In other words, the dicarboxylic acid material left after distillation was thought to be about 92% pure dicarboxylic acid. However, subsequent improvements in analytical instrumentation and techniques came to show that about 10% of what had been believed to be dicarboxylic acid was, in actuality, a C-21 lactone. This lactone was formed by the cyclization of the secondary carboxylic acid with the double bond of the cyclohexene ring. As used herein the term "lactone" is intended to mean a lactone having 21 carbon atoms (see FIG. 2). The lactonization reaction can result from the interaction of iodine with the double bond at the temperatures employed in the dicarboxylic acid synthesis.

It is difficult to remove the C-21 lactone from the dicarboxylic acid due to their structural similarity. Repeated wiped-film distillations will remove the lactone, but the procedure is costly and the final yield of purified dicarboxylic acid is extremely low.

It is also possible to purify the crude dicarboxylic acid by distillation of its methyl or dimethyl ester, as taught in U.S. Pat. No. 3,753,968. However, this procedure has proven too difficult and expensive to be feasible at a commercial scale.

Thus, no commercially feasible process had previously emerged which would produce a dicarboxylic acid of higher purity than that obtained via the method taught in U.S. Pat. No. 3,753,968—a purity of only 85%. As a consequence, the potential applications for dicarboxylic acid in the fields of lubricants, coatings, detergents, plasticizers, and corrosion inhibitors have always been limited by the presence of other substances in the reaction mixture.

Although the most extensive uses of dibasic acids are to be found in producing polymers, dicarboxylic acid (as currently produced) has little or no utility in this area. It is recognized that one needs a high percentage of chain-forming difunctional molecules in order to be able to make a high molecular weight polymer. As 15% of the current dicarboxylic acid mixture is monofunctional or trifunctional material, it is far too impure to be used in polymer production.

In the commonly assigned allowed U.S. patent application Ser. No. 07/596,021, a novel process for producing a high purity dicarboxylic acid without a catalyst is disclosed. However, the use of this process by industry would require a substantial expenditure of capital and labor for equipment not currently utilized in the standard production methods for dicarboxylic acid.

Commonly found in natural sources (an example of which is ascorbic acid or vitamin C), lactones are cyclic esters which are utilized in a variety of chemical syntheses (e.g., the Kiliani-Fischer synthesis for the conversion of an aldopentose into two aldohexoses). The C-21 lactone produced by the described process is used as an intermediate in chemical processes in the textile, surfactant, coating, and oilfield industries.

Therefore, it is the object of this invention to provide an economical process for producing both a dicarboxylic acid and a lactone of high purity. Other objects, features, and advantages will be evident from the following disclosure.

SUMMARY OF THE INVENTION

The object of this invention is met by reacting a fatty acid mixture containing linoleic acid with acrylic acid in the presence of an iodine catalyst to produce a fatty acid mixture containing dicarboxylic acid and lactone. The mixture is subsequently distilled to recover a dicarboxylic acid and lactone fraction with a low monomer content. This fraction (or feed) is subjected to double solvent extraction wherein one solvent is selected from the group consisting of hexane or heptane, and the second solvent is acetonitrile. The lactone and dicarboxylic acid are soluble in the two solvents. Although both the lactone and the dicarboxylic acid concentrate in the acetonitrile phase, the lactone concentrates at a faster rate than the dicarboxylic acid, thereby facilitating separation of the two.

By varying the solvent-to-feed ratios and/or the number of extraction stages employed, one can separate the feed into lactone and dicarboxylic acid components of varying purity. At optimum conditions, a reaction product (dissolved in the hexane or heptane solvent) can be produced which contains about 99.5% dicarboxylic acid and about 0.5% lactone. Likewise, a reaction product (dissolved in the acetonitrile solvent) can be produced which contains about 95% lactone and 5% dicarboxylic acid. The respective solvents are subsequently removed by distillation to yield the high purity dicarboxylic acid and lactone.

BRIEF DESCRIPTION OF THE DRAWINGS

The above, as well as other objects of the present invention, will become more apparent (and the invention will be better understood) from the following description of the preferred embodiments thereof, when taken together with the accompanying drawing, in which:

FIG. 3 is a diagrammatic flow plan of a multiple extraction system, with distillation, which may be employed commercially to effectively separate dicarboxylic acid and lactone from a low monomer feed mixture.

DESCRIPTION OF THE PREFERRED EMBODIMENT

The novel process that yields dicarboxylic acid and lactone of high purity first reacts fatty acids which contain linoleic acid with acrylic acid in the presence of catalytic amounts of iodine. The acrylic acid and the iodine catalyst are simultaneously added to the fatty acid mixture—the acrylic acid is added in an amount up to about 26% by weight of the fatty acid mixture, while the iodine catalyst is added in a amount of 0.01% to 0.50% by weight of the fatty acid mixture. The mixture is reacted at a temperature between 200° C. and 270° C. to convert via a Diels-Alder reaction the linoleic acid portion to a dicarboxylic acid portion (the chemical formula of which is shown in FIG. 1 below):

FIG. 1

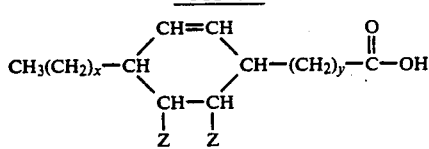

wherein X and Y are integers, X and Y together equal 12, at least one Z is a carboxylic acid group (COOH) and any remaining Z is hydrogen (H).

Also produced in the resulting mixture is a C-21 lactone having the formula:

FIG. 2

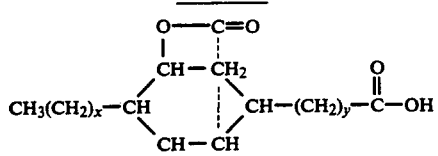

wherein X and Y are integers, and X and Y together equal 12.

This mixture is subsequently distilled via fractional column distillation, distillation on a wiped-film evaporator, or by other known methods to remove the monomers and any unreacted fatty acids from the mixture. When the mixture is sufficiently purified to contain a monomer content of 3% or less, it is suitable to serve as the feed mixture for the double solvent extraction process. Acetonitrile and hexane or heptane are the solvents employed in the process.

The efficiency of the separation of lactone and dicarboxylic acid from the feed mixture by the fractional liquid extraction process of the present invention may be expressed in terms of the ratio of the distribution coefficients (i.e., the separation factor of the two components). In fractional liquid extraction two solutes are removed from a solution by countercurrent extraction with suitable solvents. The larger the ratio of the distribution coefficients, the better the separation. The important calculations for liquid extraction of the distribution coefficients, $K_d$, $K_l$, and the separation factor, $\beta_{dl}$, of the dicarboxylic acid and lactone, respectively, are as follows:

$$K_d = \frac{\text{concentration of Dicarboxylic Acid, top phase}}{\text{concentration of Dicarboxylic Acid, bottom phase}}$$

$$K_l = \frac{\text{concentration of Lactone, top phase}}{\text{concentration of Lactone, bottom phase}}$$

$$\beta_{dl} = \frac{K_d}{K_l}$$

where the top phase contains the hexane or heptane, and the bottom phase contains the acetonitrile.

Separation, to some extent, can usually be achieved as long as the distribution coefficients are different (i.e., the separation factor $\beta_{dl}$ is greater than 1). The product of the distribution coefficients $K_d$, $K_l$ should not be far removed from unity or the low solute concentration in one of the solvents will require excessive amounts of that solvent, making for a larger solvent recovery problem.

Fatty acids which are suitable for use in this process must contain linoleic acid. Included in this list of fatty acids are: tall oil, safflower oil, corn oil, peanut oil, linseed oil, soya, and cottonseed. This list is intended to be representative, and it will be obvious to those skilled in the art that a variety of other sources of fatty acids can be used.

The following examples are provided to further illustrate the present invention and are not to be construed as limiting the invention in any manner.

EXAMPLES

The preliminary procedure that is followed is taught in commonly assigned U.S. Pat. No. 3,753,968. To L-5 (a distilled tall oil-derived fatty acid manufactured by Westvaco) is added 12% (by weight of the L-5) of acrylic acid and a catalytic amount of iodine (from 0.01% to 0.50% by weight of L-5). The mixture was heated, with stirring, to a temperature of 250° C. for a period of 3 hours.

The resulting mixture from the Diels-Alder reaction is subsequently purified on a two-inch Pope wiped film evaporator (or via other known means of distillation). The first pass, at about 200° C., serves to remove the C-18 and other monomeric materials from the dicarboxylic acid and lactone mixture as a heads product. The resulting bottoms is rerun on the evaporator at a temperature of about 280° C. to remove the heads product. This heads product is a low monomer dicarboxylic acid and lactone mixture which serves as the feed mixture for the solvent extraction.

The solvent extraction of the dicarboxylic acid and lactone components from the low monomer feed mixture may be illustrated by the following experimental single-stage laboratory extraction procedure. In the laboratory experiments conducted, the quantities of feed and solvents of each experiment were varied by volume, with acetonitrile and hexane solvents being employed in equal amounts in each laboratory procedure.

In each procedure, equal amounts of acetonitrile and hexane were placed in a separatory funnel and mixed by shaking, a quantity of low monomer feed was added to the funnel, the funnel was shaken to mix the feed and solvents, the phases were allowed to gravitationally separate, and the lower phase was withdrawn from the funnel. After separation, the phases were striped by distillation to remove the solvents, and the solutes were analyzed for lactone and dicarboxylic acid content using a gas chromatograph.

The mass of the top and bottom phases containing lactone and dicarboxylic acid was determined, and a material balance, in concentrations, was calculated. Six laboratory procedures utilizing varying amounts of feed to solvent volumetric ratios were carried out. The results thereof are set forth in Table I. Material balances and final product concentrations that were obtained for each procedure are given in Table II. The dicarboxylic acid to lactone material balance ratios are listed in Table III.

Calculations on distribution coefficients and separation factors for the six procedures are shown in Table IV.

TABLE I

Starting Quantities for Solvent Extraction

| Extraction | Solvent to Feed Ratio (by Volume) | Feed (ml) | Feed (g) | Acetonitrile (ml) | Acetonitrile (g) | Hexane (ml) | Hexane (g) |
|---|---|---|---|---|---|---|---|
| 1 | 40:1 | 10 | 10.2 | 200 | 154.68 | 200 | 129.90 |
| 2 | 30:1 | 10 | 10.2 | 150 | 116.32 | 150 | 98.00 |
| 3 | 20:1 | 10 | 10.2 | 100 | 77.34 | 100 | 64.44 |
| 4 | 15:1 | 10 | 10.2 | 75 | 58.16 | 75 | 49.00 |
| 5 | 10:1 | 10 | 10.2 | 50 | 38.70 | 50 | 32.22 |
| 6 | 5:1 | 10 | 10.2 | 25 | 19.20 | 25 | 15.60 |

TABLE II

Material Balance for Dicarboxylic Acid/Lactone Extraction

| | Feed GC % | Feed (g) | Top (g) | Bottom (g) | Loss (g) | Gain % |
|---|---|---|---|---|---|---|
| Extraction 1 S:F = 40:1 | | | | | | |
| Stream | — | 299.10 | 113.62 | 174.65 | −10.83 | −3.62 |
| Solute | | 10.00 | 3.08 | 7.44 | .52 | 5.20 |
| DA | 84.94 | 8.49 | 2.64 | 6.19 | .34 | 3.96 |
| Lactone | 8.91 | .89 | .19 | .63 | −.07 | −7.97 |
| Other | — | .62 | .25 | .62 | .25 | 41.46 |
| Solvent | | 289.10 | 110.54 | 167.21 | −11.35 | −3.93 |
| Acn | — | 157.10 | 0.00 | 157.10 | .00 | .00 |
| Hexane | — | 132.00 | 110.54 | 10.11 | −11.35 | −8.60 |
| Extraction 2 S:F = 30:1 | | | | | | |
| Stream | — | 226.90 | 86.95 | 131.95 | −8.00 | −3.53 |
| Solute | | 10.00 | 4.13 | 6.70 | .83 | 8.30 |
| DA | 84.94 | 8.49 | 3.55 | 5.52 | .58 | 6.78 |
| Lactone | 8.91 | .89 | .23 | .66 | −.00 | −.11 |
| Other | — | .62 | .35 | .52 | .26 | 41.46 |
| Solvent | | 216.90 | 82.82 | 125.25 | −8.83 | −4.07 |
| Acn | — | 117.90 | 0.00 | 117.90 | .00 | .00 |
| Hexane | — | 99.00 | 82.82 | 7.35 | −8.83 | −8.92 |
| Extraction 3 S:F = 20:1 | | | | | | |
| Stream | — | 154.60 | 59.77 | 89.49 | −5.34 | −3.45 |
| Solute | | 10.00 | 5.40 | 5.04 | .44 | 4.40 |
| DA | 84.94 | 8.49 | 4.82 | 3.96 | .29 | 3.37 |
| Lactone | 8.91 | .89 | .25 | .65 | .01 | 1.01 |
| Other | — | .62 | .33 | .43 | .14 | 23.58 |
| Solvent | | 144.60 | 54.37 | 84.45 | −5.78 | −4.00 |
| Acn | — | 78.60 | 0.00 | 78.60 | .00 | .00 |
| Hexane | — | 66.00 | 54.37 | 5.85 | −5.78 | −8.76 |
| Extraction 4 S:F = 15:1 | | | | | | |
| Stream | — | 118.40 | 46.20 | 69.40 | −2.80 | −2.36 |
| Solute | | 10.00 | 6.17 | 4.55 | .72 | 7.20 |
| DA | 84.94 | 8.49 | 5.45 | 3.58 | .54 | 6.31 |
| Lactone | 8.91 | .89 | .32 | .55 | −.02 | −2.36 |
| Other | — | .62 | .40 | .42 | .20 | 33.33 |
| Solvent | | 108.40 | 40.03 | 64.85 | −3.52 | −3.25 |
| Acn | — | 58.90 | 0.00 | 58.90 | .00 | .00 |
| Hexane | — | 49.50 | 40.03 | 5.95 | −3.52 | −7.11 |
| Extraction 5 S:F = 10:1 | | | | | | |
| Stream | — | 82.30 | 36.27 | 45.85 | −.18 | −.22 |
| Solute | | 10.00 | 7.61 | 3.00 | .61 | 6.10 |
| DA | 84.94 | 8.49 | 6.72 | 2.30 | .53 | 6.19 |
| Lactone | 8.91 | .89 | .43 | .43 | −.03 | −3.48 |
| Other | — | .62 | .46 | .27 | .12 | 18.70 |
| Solvent | | 72.30 | 28.66 | 42.85 | −.79 | −1.09 |
| Acn | — | 39.30 | 0.00 | 39.30 | .00 | .00 |
| Hexane | — | 33.00 | 28.66 | 3.55 | −.79 | −2.39 |
| Extraction 6 S:F = 5:1 | | | | | | |
| Stream | — | 46.10 | 23.20 | 21.12 | −1.78 | −3.86 |
| Solute | | 10.00 | 8.92 | 1.57 | .49 | 4.90 |
| DA | 84.94 | 8.49 | 7.93 | 1.11 | .55 | 6.43 |
| Lactone | 8.91 | .89 | .42 | .28 | −.19 | −21.44 |
| Other | — | .62 | .57 | .18 | .14 | 21.95 |
| Solvent | | 36.10 | 14.28 | 19.55 | −2.27 | −6.29 |
| Acn | — | 19.60 | 0.00 | 19.60 | .00 | .00 |
| Hexane | — | 16.50 | 14.28 | −.05 | −2.27 | −13.76 |

DA = dicarboxylic acid.
Acn = acetonitrile.

TABLE III

Dicarboxylic Acid/Lactone Material Balance

| | Ratio (Bot/Top) | | % of Starting Material | | | |
|---|---|---|---|---|---|---|
| S:F | D | L | D-Bot | D-Top | L-Bot | L-Top |
| 5:1 | .14 | .67 | .13 | .93 | .31 | .47 |
| 10:1 | .34 | 1.00 | .27 | .79 | .48 | .48 |
| 15:1 | .66 | 1.72 | .42 | .64 | .62 | .36 |
| 20:1 | .82 | 2.60 | .47 | .57 | .73 | .28 |
| 30:1 | 1.55 | 2.87 | .65 | .42 | .74 | .26 |
| 40:1 | 2.34 | 3.32 | .73 | .31 | .71 | .21 |

TABLE IV

Distribution Coefficients and Separation Factors

| Extraction | Solvent-to-Feed Ratio | $K_d$ | $K_l$ | $\beta_{dl}$ |
|---|---|---|---|---|
| 1 | 40 | .572 | .412 | 1.39 |
| 2 | 30 | .855 | .462 | 1.85 |
| 3 | 20 | 1.61 | .515 | 3.13 |
| 4 | 15 | 2.05 | .775 | 2.65 |
| 5 | 10 | 3.34 | 1.15 | 2.91 |
| 6 | 5 | 6.33 | 1.34 | 4.72 |

$K_d = \dfrac{\text{concentration of Dicarboxylic Acid, top phase}}{\text{concentration of Dicarboxylic Acid, bottom phase}}$ $K_l = \dfrac{\text{concentration of Lactone, top phase}}{\text{concentration of Lactone, bottom phase}}$ $\beta_{dl} = \dfrac{K_d}{K_l}$ where the top phase contains the hexane or heptane, and the bottom phase contains the acetonitrile.

The above results of the experimental laboratory procedure for solvent extraction of dicarboxylic acid and lactone from the low monomer reaction product of iodine catalysis of acrylic acid and fatty acid (which contains linoleic acid) can be used to calculate (by known methods) the optimum solvent to feed ratios and the minimum number of theoretical stages of separation necessary to produce the desired purities of end products utilizing commercially available multi-stage extraction column equipment. For example, by reference to data in the *Chemical Engineer's Handbook* by R. H. Perry and C. H. Chilton, Fifth Edition, p. 15–23 (which is hereby incorporated by reference), at 100 pounds per hour feed rate of the low monomer mixtures containing about 90.4% dicarboxylic acid and 9.6% lactone, it was calculated that at a solvent to feed ratio of 5:1 (with about 3.167 times more hexane than acetonitrile) a minimum of 14 theoretical stages of separation in the extraction column would be required to obtain a 99.5% pure dicarboxylic acid product and a 95% pure lactone product. A schematic of this extraction process is shown in FIG. 3 below.

FIG. 3
SCHEMATIC OF EXTRACTION PROCESS FOR PRODUCTION OF DICARBOXYLIC ACID AND LACTONE

For a basis of 100 lb/hr Dicarboxylic Acid Feed

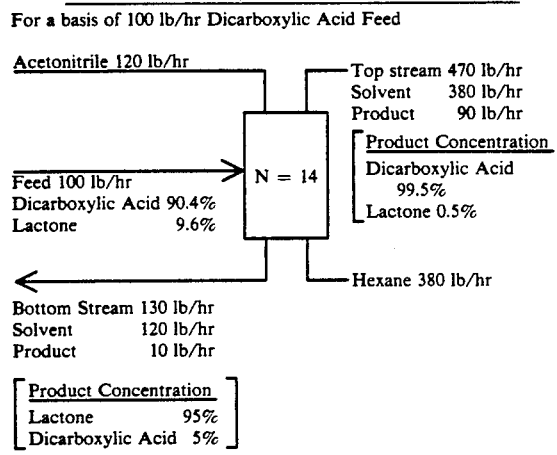

N = Minimum number of theoretical stages necessary for separation.

Many modifications and variations of the present invention will be apparent to one of ordinary skill in the art in light of the above teachings. It is therefore understood that the scope of the invention is not to be limited by the foregoing description, but rather is to be defined by the claims appended hereto.

What is claimed is:

1. In a process for the production of a 21-carbon dicarboxylic acid capable of being distilled to a purity of at least 95% and of a 21-carbon lactone capable of being distilled to a purity of at least 90%, which comprises reacting in a Diels-Alder reaction a fatty acid mixture containing linoleic acid simultaneously with up to 26% by weight of the fatty acids of acrylic acid and with from 0.01% to 0.50% by weight of said fatty acids of an iodine catalyst, at a temperature between 200° C. and 270° C., to convert said fatty acid mixture into a reaction product containing a dicarboxylic acid portion and a lactone portion wherein the improvement comprises:
   (a) isolating a purified product mixture containing up to 3% monomers from said reaction product via distillation;
   (b) fractionally extracting said purified product mixture via contact with a two component solvent system comprising a first solvent selected from the group consisting of hexane and heptane, and a second solvent of acetonitrile;
   (c) removing and separating into the respective component solvents the dicarboxylic acid and the lactone solutes; and
   (d) subsequently distilling to separate the solutes from their solvents.

2. A process as defined in claim 1 wherein the isolation of the purified product mixture comprises a first distillation at a temperature range of 150° C. to 300° C. to remove the distillate including C-18 and other monomeric materials from the reaction product, and a second distillation at a temperature range of 150° C. to 300° C. to remove the purified product mixture as a distillate from the bottoms residue containing residual dimer and trimer fatty acids.

3. A process as defined in claim 2 wherein the isolation of the purified product mixture comprises a first distillation at a temperature range of 190° C. to 220° C. to remove the distillate including C-18 and other monomeric materials from the reaction product, and a second distillation at a temperature range of 270° C. to 290° C. to remove the purified product mixture as a distillate from the bottoms residue containing residual dimer and trimer fatty acids.

* * * * *